US009357931B2

(12) United States Patent
Nahm et al.

(10) Patent No.: US 9,357,931 B2
(45) Date of Patent: *Jun. 7, 2016

(54) MEDICAL SYSTEMS AND METHODS

(71) Applicant: Carl Zeiss Meditec AG, Jena (DE)

(72) Inventors: Werner Nahm, Buehlerzell (DE);
Roland Guckler, Aalen-Dewangen (DE); Thomas Holzhauer, Essingen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/704,348

(22) Filed: May 5, 2015

(65) Prior Publication Data
US 2015/0230715 A1 Aug. 20, 2015

Related U.S. Application Data

(60) Division of application No. 13/411,973, filed on Mar. 5, 2012, now Pat. No. 9,129,366, which is a continuation of application No. 12/331,874, filed on Dec. 10, 2008, now Pat. No. 8,144,958.

(60) Provisional application No. 61/191,748, filed on Sep. 11, 2008.

(51) Int. Cl.
*G06K 9/00* (2006.01)
*A61B 5/02* (2006.01)
*A61B 5/00* (2006.01)
*A61M 5/00* (2006.01)
*A61B 17/08* (2006.01)

(52) U.S. Cl.
CPC ............. *A61B 5/02014* (2013.01); *A61B 5/004* (2013.01); *A61B 5/0071* (2013.01); *A61B 5/4836* (2013.01); *A61B 5/7425* (2013.01); *A61B 17/083* (2013.01); *A61M 5/007* (2013.01); *A61B 2576/02* (2013.01)

(58) Field of Classification Search
None
See application file for complete search history.

(56) References Cited

U.S. PATENT DOCUMENTS

| 5,125,730 A | 6/1992 | Taylor et al. |
| 5,158,090 A | 10/1992 | Waldman et al. |
| 5,240,006 A | 8/1993 | Fujii et al. |
| 5,279,298 A | 1/1994 | Flower |
| 5,291,886 A | 3/1994 | Katayama et al. |
| 5,394,199 A | 2/1995 | Flower |
| 5,675,378 A | 10/1997 | Takasugi et al. |

(Continued)

FOREIGN PATENT DOCUMENTS

| DE | 19539829 | 4/1997 |
| DE | 19635038 | 3/1998 |

(Continued)

OTHER PUBLICATIONS

Wrobel, Charles J., et al. "Intraoperative assessment of aneurysm clip placement by intravenous fluorescein angiography." Neurosurgery 35.5 (1994): 970-973.*

*Primary Examiner* — Li Liu
(74) *Attorney, Agent, or Firm* — Fish & Richardson P.C.

(57) ABSTRACT

This disclosure generally relates to medical systems and methods. In one aspect of the invention, a method includes determining a fluorescent light intensity at one or more points on each of multiple recorded images, and producing an image based on the determined fluorescent light intensity at the one or more points.

20 Claims, 9 Drawing Sheets

(56) References Cited

U.S. PATENT DOCUMENTS

| | | | |
|---|---|---|---|
| 5,697,885 A | 12/1997 | Konomura et al. | |
| 5,822,446 A * | 10/1998 | Kato | G06F 19/321 |
| | | | 382/128 |
| 5,934,278 A | 8/1999 | Ishihara et al. | |
| 6,223,069 B1 | 4/2001 | Pfeiffer et al. | |
| 6,351,663 B1 | 2/2002 | Flower et al. | |
| 6,540,688 B1 | 4/2003 | Gingrich et al. | |
| 6,554,775 B1 | 4/2003 | Peyman et al. | |
| 6,569,104 B2 | 5/2003 | Ono et al. | |
| 6,631,286 B2 | 10/2003 | Pfeiffer et al. | |
| 6,853,857 B2 | 2/2005 | Pfeiffer et al. | |
| 6,944,493 B2 | 9/2005 | Alam et al. | |
| 7,113,817 B1 | 9/2006 | Winchester et al. | |
| 7,400,753 B2 | 7/2008 | Seino et al. | |
| 7,529,576 B2 | 5/2009 | Keller et al. | |
| 8,144,958 B2 | 3/2012 | Nahm et al. | |
| 9,129,366 B2 | 9/2015 | Nahm et al. | |
| 2002/0099279 A1 | 7/2002 | Pfeiffer et al. | |
| 2002/0102013 A1 | 8/2002 | Smilansky | |
| 2002/0102213 A1 | 8/2002 | Sutoo et al. | |
| 2002/0183621 A1 | 12/2002 | Pfeiffer et al. | |
| 2003/0044054 A1 | 3/2003 | Olschewski et al. | |
| 2003/0060718 A1 | 3/2003 | Alam et al. | |
| 2004/0022449 A1 | 2/2004 | Olschewski | |
| 2004/0109231 A1 | 6/2004 | Haisch et al. | |
| 2004/0142485 A1 | 7/2004 | Flower et al. | |
| 2004/0162492 A1 | 8/2004 | Kobayashi | |
| 2004/0249275 A1 | 12/2004 | Keller et al. | |
| 2005/0182434 A1 * | 8/2005 | Docherty | A61B 1/042 |
| | | | 606/170 |
| 2005/0241653 A1 | 11/2005 | Van Heugten et al. | |
| 2006/0033042 A1 | 2/2006 | Groezinger et al. | |
| 2006/0161063 A1 | 7/2006 | Shau | |
| 2006/0188402 A1 | 8/2006 | Xie et al. | |
| 2006/0285738 A1 | 12/2006 | Boese et al. | |
| 2007/0260137 A1 | 11/2007 | Sato et al. | |
| 2008/0013166 A1 | 1/2008 | Haisch et al. | |
| 2008/0015446 A1 | 1/2008 | Mahmood et al. | |
| 2008/0045848 A1 | 2/2008 | Lacombe et al. | |
| 2008/0212867 A1 | 9/2008 | Provenzano et al. | |
| 2009/0252414 A1 | 10/2009 | Suzuki | |
| 2010/0041999 A1 | 2/2010 | Schuhrke et al. | |
| 2010/0061604 A1 | 3/2010 | Nahm et al. | |
| 2012/0165662 A1 | 6/2012 | Nahm et al. | |
| 2015/0230710 A1 | 8/2015 | Nahm et al. | |
| 2015/0230711 A1 | 8/2015 | Nahm et al. | |

FOREIGN PATENT DOCUMENTS

| | | |
|---|---|---|
| DE | 10059070 | 2/2002 |
| DE | 10120980 A1 | 11/2002 |
| DE | 69332205 | 12/2002 |
| DE | 10143441 A1 | 3/2003 |
| DE | 69529245 T2 | 8/2003 |
| DE | 69431890 | 11/2003 |
| DE | 10235657 A1 | 2/2004 |
| DE | 10339784 | 3/2004 |
| DE | 10257743 | 7/2004 |
| DE | 10315574 | 10/2004 |
| DE | 69433413 | 10/2004 |
| DE | 69434555 | 8/2006 |
| DE | 10 2005 022 541 A1 | 12/2006 |
| DE | 10 2005 027 678 A1 | 12/2006 |
| DE | 102005044531 | 3/2007 |
| DE | 102006006014 | 9/2007 |
| EP | 669819 | 9/1995 |
| EP | 801534 | 10/1997 |
| EP | 0 387 793 B1 | 1/1998 |
| EP | 928156 | 7/1999 |
| EP | 1084675 | 3/2001 |
| EP | 1210906 | 6/2002 |
| EP | 1464276 | 10/2004 |
| EP | 1485007 | 12/2004 |
| EP | 1 568 307 A1 | 8/2005 |
| EP | 1 679 035 A1 | 7/2006 |
| EP | 1 254 630 B1 | 2/2007 |
| EP | 1084674 | 3/2007 |
| EP | 1 768 563 A1 | 4/2007 |
| EP | 1 143 852 B1 | 10/2007 |
| EP | 1852057 | 11/2007 |
| EP | 1 861 000 A1 | 12/2007 |
| EP | 1 864 608 A1 | 12/2007 |
| EP | 1 880 657 A1 | 1/2008 |
| JP | 3715311 | 11/2005 |
| JP | 2005-354201 A1 | 12/2005 |
| JP | 2006-204618 A1 | 8/2006 |
| JP | 2008-501457 A1 | 1/2008 |
| WO | WO 94/12092 | 6/1994 |
| WO | WO 96/09792 | 4/1996 |
| WO | WO 98/08434 | 3/1998 |
| WO | WO 01/17561 | 3/2001 |
| WO | WO 03/057259 | 7/2003 |
| WO | WO 03/077741 | 9/2003 |
| WO | WO 2004/052195 | 6/2004 |
| WO | WO 2005/120352 A1 | 12/2005 |
| WO | WO 2006/097866 A1 | 9/2006 |
| WO | WO 2006/111909 A1 | 10/2006 |
| WO | WO 2007/090591 | 8/2007 |

* cited by examiner

MEDICAL SYSTEMS AND METHODS

CROSS-REFERENCE TO RELATED APPLICATIONS

This application is a division of, and claims priority under 35 USC to U.S. application Ser. No. 13/411,973, filed Mar. 5, 2012, which is a continuation of, and claims priority under 35 USC 120 to, U.S. application Ser. No. 12/331,874, filed Dec. 10, 2008, which claims the benefit of U.S. application Ser. No. 61/191,748, filed on Sep. 11, 2008. The contents of these applications are hereby incorporated by reference in its entirety.

TECHNICAL FIELD

This disclosure relates to medical systems and methods.

BACKGROUND

Neuro-surgical therapy is a technique that can be used to treat an aneurysm, i.e., a sac shaped localized enlargement of the cross-section of a patient's artery. During neuro-surgical therapy, a clip is typically used to clamp off the aneurysm from the blood circulation. Neuro-surgical therapy can decrease the likelihood of the aneurysm rupturing.

To determine whether the aneurysm sac has been completely closed with the clip and whether the blood flows properly in other arterial vessels in close proximity to the clip, a fluorescent dye can be administered intravenously to the patient and the flow of the dye into the artery can be observed through a camera. If the blood mixed with the fluorescent dye is visible in the aneurysm sac, this indicates that the aneurysm sac was not completely closed with the clip. Similarly, if the blood mixed with the fluorescent dye is not visible in certain regions of the artery until after a delay, this can indicate that those regions of the artery are least partially blocked.

SUMMARY

In one aspect of the invention, a method includes determining a fluorescent light intensity at one or more points on each of multiple images of tissue of a subject and producing an image based on the determined fluorescent light intensity at the one or more points.

In another aspect of the invention, a method includes recording multiple images of a region of a blood vessel, analyzing the multiple recorded images to determine a maximum fluorescent light intensity at multiple points on each of the recorded images, and displaying an image that represents the maximum fluorescent light intensity at each of the multiple points.

In an additional aspect of the invention, a method includes recording multiple images of a region of a blood vessel, analyzing the multiple images to determine a time at which a predetermined fluorescent light intensity was reached for each of multiple points on each of the recorded images, and displaying an image that represents a relative amount of time for each point to reach the predetermined fluorescent light intensity.

In a further aspect of the invention, a method includes recording multiple images of a region of a blood vessel, analyzing the multiple recorded images to determine a fluorescent light intensity at each of multiple points on each of the recorded images, and displaying an image that represents the fluorescent light intensity for each of the multiple points over a period of time.

In another aspect of the invention, a method of treating an aneurysm includes: exposing an aneurysm at a surgical site; injecting a fluorescent dye into a blood vessel that includes the aneurysm; capturing a first set of images of the surgical site with a camera; analyzing the first set of images captured by the camera in a signal processing and analysis unit; applying a clip to the aneurysm to clamp off the aneurysm; after applying the clip to the aneurysm, capturing a second set of images of the surgical site with the camera; analyzing the second set of images captured by the camera in a signal processing and analysis unit; and comparing the first set of images with the second set of images to determine the effectiveness of the clip to clamp of the aneurysm.

In an additional aspect of the invention, a system includes a computer system with a processor for executing instructions and memory storing a computer program product which, when executed by the processor, performs a method that includes determining a fluorescent light intensity at one or more points on each of multiple images of tissue of a subject and producing an image based on the determined fluorescent light intensity at the one or more points.

In a further aspect of the invention, a system includes a computer program product capable of determining a fluorescent light intensity at one or more points on each of multiple images of tissue of a subject and producing an image based on the determined fluorescent light intensity at the one or more points.

Embodiments can include one or more of the following features.

In some embodiments, the method further includes recording the multiple images of the tissue of the subject.

In certain embodiments, determining the fluorescent light intensity at the one or more points on each of the multiple images involves analyzing each of the multiple images.

In some embodiments, the method further includes displaying the image based on the determined fluorescent light intensity at the one or more points.

In certain embodiments, determining the fluorescent light intensity at the one or more points on each of the multiple images involves determining a maximum fluorescent light intensity at the one or more points on each of the multiple images.

In some embodiments, the image that is produced based on the determined fluorescent intensity at the one or more points is a representation of the maximum fluorescent intensity determined at the one or more points.

In certain embodiments, the one or more points on each of the multiple images includes multiple points on each of the multiple images.

In some embodiments, the maximum fluorescent light intensity at each of the multiple points is represented by a brightness, and the brightness increases as the maximum fluorescent light intensity increases.

In certain embodiments, the method further includes determining a time at which a predetermined fluorescent light intensity was reached at each of the one or more points.

In some embodiments, the image that is produced based on the determined fluorescent intensity at the one or more points represents an amount of time for each of the one or more points to reach the predetermined fluorescent light intensity after introducing a fluorescent substance into the tissue of the subject.

In certain embodiments, the amount of time required for each of the one or more points to reach the predetermined fluorescent light intensity after introducing the fluorescent substance into the tissue of the subject is represented by a color on the produced image.

In some embodiments, the one or more points on each of the multiple images includes multiple points on each of the multiple images.

In certain embodiments, the greatest amount of time required to reach the predetermined fluorescent light intensity among the multiple points is represented as a first color, and the least amount of time required to reach the predetermined fluorescent light intensity among the multiple points is represented as a second color that is different than the first color.

In some embodiments, times to reach the predetermined fluorescent light intensity that are between the greatest amount of time and the least amount of time are represented by a combination of the first and second colors.

In certain embodiments, the image that is produced based on the determined fluorescent intensity at the one or more points includes a graph illustrating the determined fluorescent intensity at the one or more points over a period of time.

In some embodiments, the one or more points on each of the multiple images comprises multiple points on each of the multiple images.

In certain embodiments, the multiple images of the tissue of the subject are recorded by a camera.

In some embodiments, the multiple images of the tissue of the subject are analyzed by a microprocessor connected to the camera.

In certain embodiments, the image based on the determined fluorescent light intensity at the one or more points is displayed by a screen connected to the microprocessor.

In some embodiments, the tissue of the subject includes a blood vessel of the subject.

In certain embodiments, the method further includes introducing a fluorescent substance into the blood vessel.

In some embodiments, the method further includes applying light having a wavelength of 400 nm to 780 nm to the blood vessel.

In certain embodiments, the multiple images are recorded with a fluorescent light camera.

In some embodiments, the multiple images are analyzed by a processor.

In certain embodiments, the method further includes transmitting the multiple images from a camera to the processor.

In some embodiments, the multiple points on each of the multiple images includes all of the points on each of the multiple images.

In certain embodiments, the method further includes treating the tissue of the subject.

In some embodiments, the multiple images are images of the tissue of the subject before the tissue of the subject is treated.

In certain embodiments, the method further includes determining a fluorescent light intensity at one or more points on each of a second multiple images of the tissue of the subject after treatment of the tissue of the subject, and producing an image based on the determined fluorescent light intensity at the one or more points.

In some embodiments, the method further includes simultaneously displaying the produced images.

In certain embodiments, the method further includes comparing the produced images to assess the success of the treatment.

In some embodiments, the method further includes adjusting the images of the multiple images so that corresponding points on each of the images are aligned with one another.

In certain embodiments, the imaged region includes multiple blood vessels.

In some embodiments, the system further includes a camera adapted to record the multiple images of the tissue of the subject.

In certain embodiments, the system further includes a display adapted to display the image based on the fluorescent intensity at the one or more points.

In some embodiments, the processor is adapted to transmit to the display a signal containing the image based on the fluorescent intensity at the one or more points.

In certain embodiments, the processor is adapted to adjust the series of images so that corresponding points on each of the images are aligned with one another.

In some embodiments, the system further includes a fluorescent light source that can be arranged to direct fluorescent light to the site.

In certain embodiments, the system is an operating microscope.

In some embodiments, the computer program product is software.

Embodiments can include one or more of the following advantages.

In some embodiments, the methods enable a physician to check the state of blood flow through a blood vessel by viewing a single image. As compared to certain previous methods that required the physician to view a series of images to determine certain patterns of blood flow (e.g., the amount of blood flow through certain regions of the blood vessel, the amount of time required for blood flow to reach certain regions of the blood vessel, etc.), methods described herein can decrease the amount of time that it takes to determine these blood flow patterns.

In certain embodiments, the methods allow the physician to view blood flow patterns at discrete points within a blood vessel. This can provide the physician with detailed information about a specific region of a blood vessel (e.g., an aneurysm in the blood vessel). This can improve the ability of the physician to make treatment decisions or assess the success of a treatment.

In some embodiments, the systems and methods permit the physician to simultaneously view an image showing pre-treatment blood flow patterns and an image showing post-treatment blood flow patterns on a single display screen. As a result, the physician can more quickly assess the success of the treatment.

In certain embodiments, blood flow patterns are displayed as a brightness gradient or color gradient, which allows the user to quickly assess the state of blood flow. In some embodiments, for example, the user can simply determine whether a certain region of a displayed blood vessel is bright v. dark or red v. blue to assess the state of blood flow in that region. As a result, the speed and efficiency with which the assessment is performed can be increased.

Other aspects, features, and advantages will be apparent from the description and drawings, and from the claims.

DETAILED DESCRIPTION

In general, this disclosure relates to medical systems and methods. In some embodiments, the medical system includes an operating microscope that is configured to detect and display certain blood flow patterns within a blood vessel. Certain methods can, for example, include introducing a fluorescent substance (e.g., a fluorescent dye) into the blood vessel, and then using the operating microscope to measure a fluorescent light intensity in a particular region of the blood vessel (e.g., in a region of the blood vessel including an aneurysm). In certain embodiments, the operating microscope records a series of images of the blood vessel region, analyzes those images, and then produces a single image that summarizes blood flow patterns that occurred within the blood vessel region over the series of images. As a result, the physician can assess blood flow within the blood vessel region by analyzing a single image rather than a series of images. In addition, the physician may observe certain blood flow patterns that would not be easily detected by simply viewing the series of images recorded by the microscope.

Figure 1:
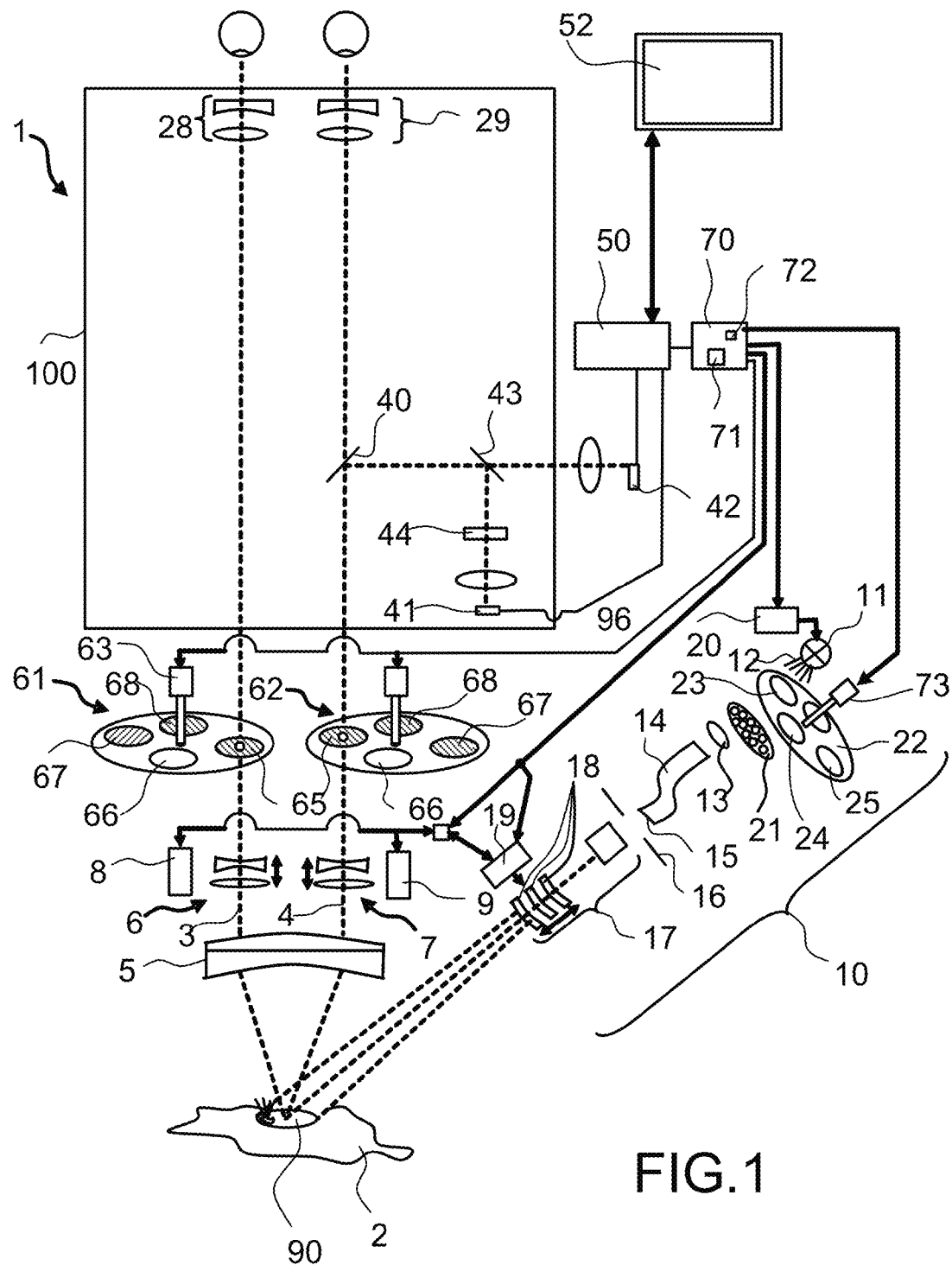
FIG. 1 is a schematic of an operating microscope system.

FIG. 1 is a schematic of an operating microscope 1 that is arranged to examine a surgical site 2. The surgical site 2, which is shown and described in greater detail below, is a portion of the brain with an artery that includes an aneurysm. The operating microscope 1 can be positioned adjacent the aneurysm in the brain, as shown in FIG. 1, after a craniotomy has been performed to expose the aneurysm.

The operating microscope includes a lighting system 10 that illuminates the surgical site 2, causing stereoscopic viewing beams 3, 4 to pass though a main lens 5. The viewing beams 3, 4 then pass through optical zoom systems 6, 7, which include powered actuating drives 8, 9 that can be used to adjust the magnification of the viewing beams 3, 4. The viewing beams 3, 4 then pass through aperture/filter disks 61, 62 that can be used to adjust the amount of light that passes therethrough. After passing through the aperture/filter disks 61, 62, the viewing beams 3, 4 are directed to eyepieces 28, 29 through which the surgeon can view the surgical site 2. The viewing beam 4 is also directed by beam dividers 40 and 43 to a fluorescent camera 41 and by a beam divider 40 to a camera 42.

Prior to reaching the camera 41, the divided viewing beam 4 passes through a filter 44 transparent to fluorescent light. The filter 44 can, for example, be designed to permit fluorescent light to pass therethrough while blocking other forms of light. The camera 41 detects the fluorescent light emitted from the surgical site 2, which is delivered to the camera 41 in the viewing beam 4, and records images of the surgical site 2 based on the detected fluorescent light pattern. The camera 41 is adapted to record both continuous video of the surgical site 2 and periodic images of the surgical site 2. In addition to the continuous video, for example, the camera 41 can record an image (e.g., a half image) of the surgical site 2 every 120 ms. As described in greater detail below, fluorescent light can be emitted from the surgical site 2 by injecting a fluorescent dye into the surgical site and then contacting the fluorescent dye with light having a wavelength that causes the fluorescent dye to fluoresce. This technique permits the surgeon to view blood flowing through vessels within the surgical site 2 rather than simply the outside of vessels and other matter at the surgical site 2. The camera 41 can transmit a signal or signals containing a continuous video and a series of discrete images of the surgical site 2 to a signal processing and analysis unit 50. The continuous video can be transmitted from the signal processing and analysis unit 50 to the touch screen 52 were it is displayed for the surgeon. In addition, the signal processing and analysis unit 50 can analyze the series of images and produce a single image, based on the analysis of the series of images, that represents certain blood flow patterns within the surgical site over time. The signal processing and analysis unit 50 can transmit the produced image in the form of a data signal to a touch screen 52 of the operating microscope 1 where it can be displayed for the surgeon to view.

The camera 42 is also connected to the signal processing and analysis unit 50. The camera 42 is adapted to record images of the exterior of the surgical site 2 and to transmit those images in the form of a signal to the signal processing and analysis unit 50. The camera 42 can record continuous video of the surgical site 2 and/or a series of separate images of the surgical site 2. The images of the surgical site 2 recorded by the camera 42 can be displayed on the touch screen 52 by transmitting a signal containing the images from the signal processing and analysis unit 50 to the touch screen 52.

The lighting system 10 of the operating microscope 1 includes a Xenon lamp 11, which, when activated, emits light 12 that passes through a filter disk 22. The filter disk 22 includes multiple different filters 23, 24, and 25 that enable the lighting system 10 to illuminate the surgical site 2 with light having a desired range of wavelengths while inhibiting (e.g., preventing) light with wavelengths outside the desired range from being delivered to the surgical site 2. By rotating the filtering disk 22, the desired filter can be pivoted into the path of the light beam for a desired viewing mode.

The filter 23 is provided for situations in which the surgeon wishes to view the surgical site 2 without fluorescent light. The filter 23 can, for example, be used when the surgeon wishes to view the surgical site 2 through the eyepieces 28, 29 and when the user wishes to view images taken by the camera 42 on the touch screen 52. Filter 23 is a bandpass filter, which is transparent for light with a wavelength of 400 nm<$\lambda$<700 nm in the visible part of the spectrum. Filter 23 helps to reduce (e.g., prevent) stress on the surgical site due to UV radiation and thermal radiation generated by the lamp 11 in the lighting system.

The filter 24 is designed for viewing of the surgical site 2 with fluorescent light of the fluorescent dye ICG The filter 24 is a bandpass filter, which is transparent for light with a wavelength of 400 nm<λ<780 nm in the visible spectrum. When ICG is exposed to light within this range of wavelengths it fluoresces.

The filter 25 is designed for viewing of the surgical site 2 with fluorescent light of the fluorescent dye BL 400. The filter 25 is a bandpass filter, which is transparent for light with a wavelength of 400 nm<λ<410 nm. When BL 400 is exposed to light within this range of wavelengths it fluoresces.

A screen aperture 21 with regular/random holes is also provided in the light path of the lighting system 10 for the continuous adjustment of the flow of light through the lighting system 10. After passing through the screen aperture 21, the light passes through a lens 13 and is then directed through a light guide 14. An aperture 16 with an adjustable opening is located at the exit 15 of the light guide 14. Light that passes through the aperture 16 is routed via luminous field optics 17 to the surgical site 2. By opening or closing the aperture 16, the amount of light delivered to the luminous field optics 17 can be increased or decreased. The luminous field optics 17 include an adjustable lens system 18 that can be used to adjust the size of a luminous field 90 at the surgical site 2. An actuator 19 is connected to the lens system 18 and can be used to adjust the lens system 18. By adjusting the lens system 18, the flow of light from the lighting system 10 to the surgical site 2 can be varied and focused based on desired parameters. Thus, the illumination strength in the luminous field 90 can be adjusted as desired.

A control unit 20 is connected to the lamp 11 and can be used to control the flow of light emitted by the lamp 11. The control unit 20 is also connected to an actuator 73 that is coupled to the filter disk 22 such that the control unit 20 can control which of the filters 23, 24, 25 is positioned in the beam of light emitted from the lamp 11.

The powered actuating drives 8, 9 of the zoom system can be connected to the lens system 18 via the actuator 19 such that when the zoom setting of the operating microscope 1 is changed, the size of the illuminated field 90 automatically adjusts to the size of the viewing field.

The aperture/filter disks 61, 62 can be positioned to adjust the amount of light that reaches the eyepieces 28, 29 and the cameras 41, 42. Located inside the aperture/filter disks 61, 62 are apertures 65, 66 with different size openings and filters 67, 68 with different transmission characteristics. When the aperture 65 is positioned inside the viewing paths, the operating microscope generates a relatively faint image with high definition. Positioning the aperture 66 into the viewing paths ensures a maximum flow of light to the cameras 41, 42 and to the eyepiece lenses 28, 29. To view the surgical site 2 under fluorescent light, it is advantageous for the flow of light to the camera 41 to be at a maximum level. Thus, when viewing the surgical site 2 under fluorescent light, the disks 61, 62 are generally positioned so that the viewing beams 3, 4 pass through the apertures 66 of the disks 61, 62. The disks 61, 62 are coupled to adjustable drives 63, 74 that can rotate the disks to the desired position.

As noted above, the fluorescent camera 41 is connected to the signal processing and analysis unit 50, which can produce an image based on a series of images received from the fluorescent camera 41 and can transmit that image in the form of a signal to the touch screen 52. The signal processing and analysis unit 50 is also connected to a controller 70. The controller 70 has a memory 72 in which settings related to operation of the operating microscope 1 in the fluorescent mode are stored. These settings can include, for example, settings for the current of the lamp 11, settings for the filter disk 22, settings for the screen aperture 21, settings for the adjustable lens system 18 of the illuminated field optics 17, and settings for the position of the aperture/filter disks 61, 62. When an activation switch 71 on the controller 70 is pressed, the operating microscope 1 is automatically configured for the fluorescent operating mode. For this purpose, the controller 70 is connected to a control unit 20 of the lamp 11, the actuator of the aperture/filter disk 22, the actuating drive 19 for the adjustable lens system 18, the actuating drives 8, 9 for the zoom system 6, 7, and the adjustable drives 63, 64 for the aperture/filter disks 61, 62. When the microscopy system controller 70 is activated, the controller 70 transmits signals to those devices to automatically set those devices to the values stored in the memory 72. As a result, the surgeon need not manually adjust various different components every time the operating microscope 1 is switched between the fluorescent operating mode and the standard operating mode.

A method of performing and assessing neuro-surgical repair of a brain aneurysm will now be described. Initially, a craniotomy is performed to expose the region of the artery in the brain that includes the aneurysm. This region is schematically illustrated as the surgical site 2 in FIG. 1. The operating microscope 100 is then positioned with its main lens 5 adjacent the surgical site 2 and with its lighting system 10 arranged to shine light onto the surgical site 2, as shown in FIG. 1. After positioning the operating microscope as desired, the lighting system 10 is activated to shine light with a desired wavelength on the exposed artery to allow the surgeon to view the brain aneurysm in a desired manner. The wavelength of the light to which the surgical site 2 is exposed can, as discussed above, be controlled by adjustments to the filter disk 22 of the lighting system 10. Initially, the surgeon can view the surgical site 2 in a standard mode (i.e., a non-fluorescent mode) such that the surgeon can view the exterior of the artery with the aneurysm. The surgeon can view the surgical site 2 through the eyepieces 28, 29 or can view images of the surgical site 2 on the touch screen 52. In this standard mode, for example, the camera 42 can record images of the surgical site 2 and transmit those images to the touch screen 52 via the signal processing and analysis unit 50 for display.

Figure 2:
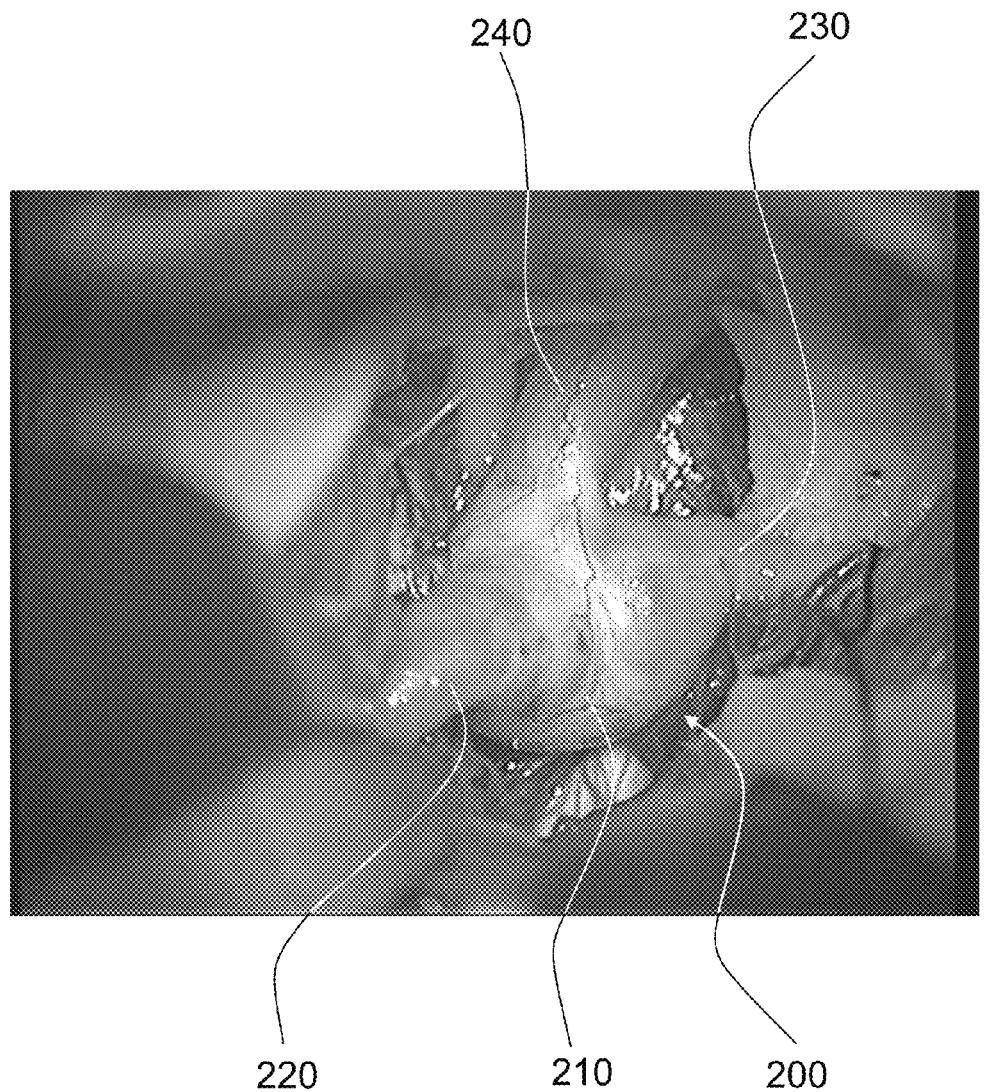
FIG. 2 is an image of a blood vessel with an aneurysm, as viewed through the operating microscope of FIG. 1.

FIG. 2 shows the surgical site 2, as viewed through the operating microscope 100 of FIG. 1 in the standard mode. As shown, the surgical site 2 includes an artery 240 with an aneurysm 200 that includes an aneurysm sac 210 with evaginations 220 and 230.

Prior to repairing the aneurysm 200, the surgeon can use the operating microscope 100 in a fluorescent mode to view blood flow patterns within the artery 240. As discussed below, these blood flow patterns can subsequently be compared with blood flow patterns through the artery 240 after repairing the aneurysm 200 to allow the surgeon to assess the success of the treatment.

To view blood flow patterns within the artery 240, the switch 71 on the controller 70 is activated to place the operating microscope 1 in the fluorescent mode. As a result, the controller 70 transmits signals to the various devices of the operating microscope 1 to which the controller 70 is connected to make any desired adjustments to those devices. A fluorescent dye (e.g., ICG) is then intravenously injected into the bloodstream in the artery 240 upstream of the aneurysm 200. The fluorescent dye can, for example, be introduced into the bloodstream over a period of 0.5 second to several seconds (e.g., 0.5 second to two seconds). The lighting system 10, which was automatically adjusted by the controller 70, transmits the light 12 at a wavelength that causes the fluorescent dye within the artery 240 to fluoresce. As a result, those portions of the artery 240 that are supplied with blood (and thus supplied with the fluorescent dye) will generate fluorescent light. The fluorescent light emitted from the fluorescent dye within the artery 240 passes through the main lens 5 and the zoom system 7 and is directed to the camera 41 by the beam dividers 40 and 43. A continuous video of the surgical site 2 is recorded by the camera 41 and transmitted to the signal processing and analysis unit 50. The continuous video of the surgical site 2 can be immediately displayed on the touch screen 52 for the surgeon to view in real time. While recording the continuous video, a series of fluorescent images of the surgical site 2 are also recorded by the camera 41 and transmitted in the form of signals from the camera 41 to the signal processing and analysis unit 50 where they are stored. The signal processing and analysis unit 50 analyzes the images and produces a single image that summarizes the flow pattern within the artery 240. A signal containing the image produced by the signal processing and analysis unit is then transmitted to the touch screen 52 where the image is displayed.

The type of image that is produced within the signal processing and analysis unit 50 and then displayed on the touch screen 52 can be chosen by the surgeon by selecting a desired button on the touch screen 52. For example, the user can select a button that causes the signal processing and analysis unit 50 to produce an image that shows a spatial distribution of the maximum intensity of fluorescent light across the surgical site 2, a button that causes the signal processing and analysis unit 50 to produce a spatial image of the change over time of the fluorescent light intensity across the surgical site 2, and/or a button that causes the signal processing and analysis unit 50 to produce an image of the intensity of fluorescent light over time at selected locations of the surgical site 2.

Figure 3:
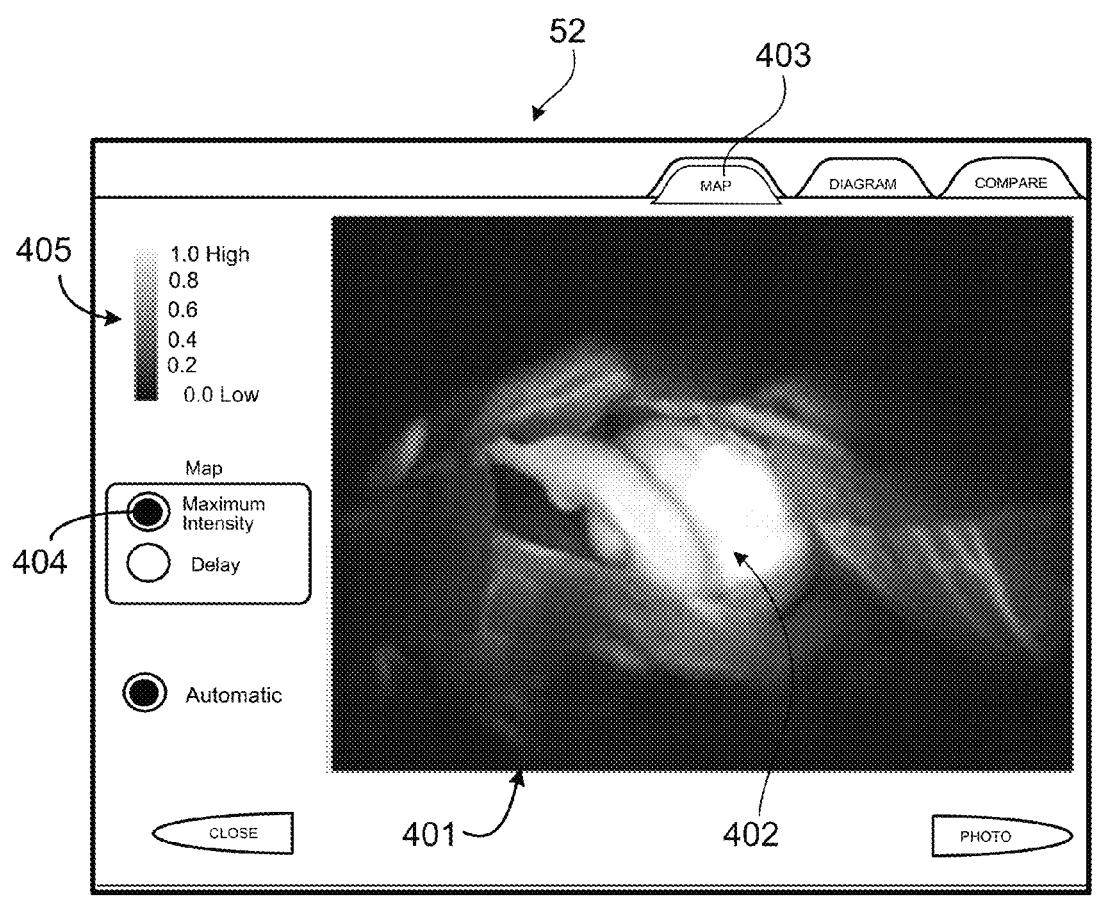
FIG. 3 illustrates a display screen of the operating microscope of FIG. 1, displaying a spatial distribution of the maximum intensity of fluorescence light in the blood vessel region shown in FIG. 2.

FIG. 3 is a screen shot of the touch screen 52. As shown, a Map tab 403 has been selected and the surgeon has opted to view the maximum intensity of the fluorescent light in the imaged region by selecting a Maximum Intensity button 404. As a result of these selections, the signal analysis and processing unit 50 analyzes each point (e.g., each pixel) on the series of images transmitted to it by the fluorescent camera 41 and identifies the maximum fluorescent intensity that occurred at each point over the series of images. The signal analysis and processing unit 50 then produces an image that depicts the surgical site 2 based on the maximum fluorescent intensity that was observed at each point in the surgical site 2. That image is then transmitted in the form of a signal to the touch screen 52 where it is displayed in a display field 401. As indicated on the brightness scale 405, the highest fluorescent intensity recorded at the target site is shown as being brightest, the lowest fluorescent intensity recorded at the target site is shown as being darkest, and intermediate intensities are shown as having varying levels of brightness therebetween depending on their intensities.

Still referring to FIG. 3, the aneurysm 402 at the surgical site is shown as having about the highest fluorescent light intensity in the surgical site. This is because the concentration of the fluorescent dye is greatest in those regions of the surgical site through which relatively large amounts of blood flow. In contrast to the brightly-displayed aneurysm 402, tissue regions that surround the artery and receive less blood are shown as being darker. Thus, by looking at this image, the surgeon can quickly determine the local density distribution of blood at the surgical site, which can help the surgeon to determine the severity of the aneurysm and the supply of blood to the aneurysm.

A motion compensation technique can be applied to the captured images by the signal processing and analysis unit 50 before determining the maximum intensities. Such a technique can improve the sharpness and reduce blurriness of the images. The motion compensation uses an edge detection process to generate edge images of the individual images in order to correlate them and to thus determine the alignment vector. This procedure allows the correlation of the edge image of an individual image with a respective reference image. The reference image is then developed further by being complemented by the "misaligned" actual edge image. The signal processing and analysis unit 50 can, for example, analyze a region of the image displaying the edge of the artery 400 and surrounding tissue. The demarcation between the edge of the artery 400 and the surrounding tissue, which will show up as a much different light pattern in the images, can be used as a reference point for subsequent images. In particular, the signal processing and analysis unit 50 can adjust subsequent images to ensure that the demarcation between the artery 400 and the surrounding tissue in those images is positioned at the same location as it is in the reference image. This will help to ensure that specific features of the surgical site show up at the same location on each of the images analyzed by the signal analysis and processing unit 50. As a result, the analysis performed by the signal processing and analysis unit 50 will be accurate even if the operating microscope 1 experiences some movement during the procedure.

Before determining the maximum intensities, a brightness correction is also applied to the individual images. In order to make this possible, the information required for the brightness correction is recorded and stored as meta data together with the captured images. Any of various know gain control techniques can be used to correct or adjust the brightness of the various images.

Figure 4:
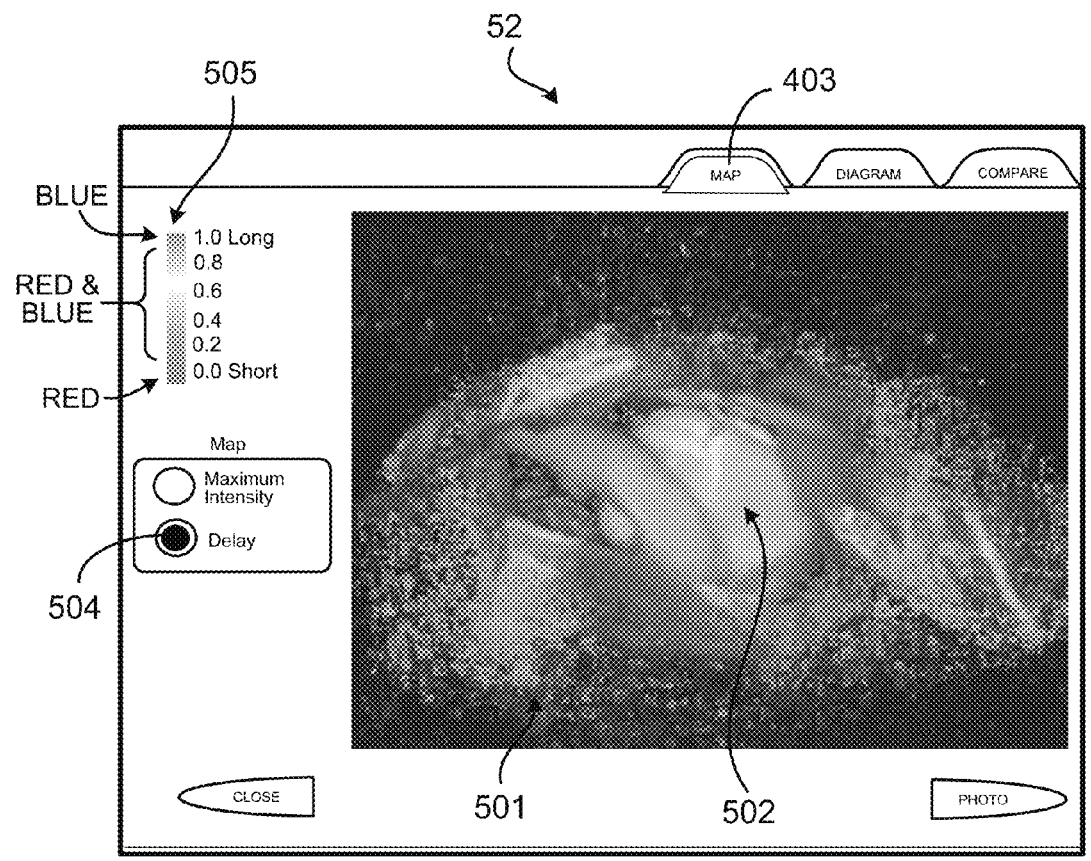
FIG. 4 illustrates the display screen of the operating microscope of FIG. 1, displaying an image representing the different rates at which the fluorescent light intensity changes over time in the blood vessel region shown in FIG. 2.

FIG. 4 is another screen shot of the touch screen 52. As shown, the Map tab 403 has been selected and the surgeon has opted to view the rate at which the various points in the imaged region reach a threshold fluorescent light intensity by selecting the Delay button 504. As a result of these selections, the signal analysis and processing unit 50 analyzes each point (e.g., each pixel) on the series of images transmitted to it by the fluorescent camera 41 and determines the period of time that it took for each of those points to reach the threshold fluorescent light intensity. The operating microscope 1 then displays on the touch screen 52 a false color image that represents the amount of time that it took the various points of the surgical site to reach the threshold fluorescent light intensity.

To determine the change in the fluorescent light intensity over time, the signal processing and analysis unit 50 compares the fluorescent intensity experienced at each point on the series of images to the threshold intensity value. The threshold intensity value can, for example, be 50 percent of the maximum fluorescent intensity recorded at the particular point being analyzed. Any of various other threshold intensity values can alternatively be used. In certain cases, for example, the threshold intensity value is 20 percent of the maximum fluorescent light intensity. In order to determine the threshold value for each point or area to be viewed, a brightness graph of the signal can be produced within the signal processing and analysis unit 50 and then the signal processing and analysis unit 50 can determine at which point in time the threshold intensity value was reached. The signal transmitted from the camera 41 to the signal processing and analysis unit 50 can, for example, include information related to the time that each image was recorded in addition to the information related to the fluorescent intensity of the image to allow the signal processing and analysis unit 50 to compare the points in time at which each of the various points reached the threshold intensity value.

Still referring to FIG. 4, the relative time that it takes for each point to reach the threshold intensity value is displayed as a false color image in display field 501. As indicated on the brightness scale 505, the point or points that experienced the shortest time period to reach the threshold intensity value is/are shown in red, the point or points that experienced the longest time period to reach the threshold intensity value is/are shown in blue, and the point or points that experienced intermediate time periods to reach the threshold intensity are shown as a combination of blue and red. Thus, regions of the surgical site that have good blood flow and thus are supplied with blood early will typically be shown nearer the red end of the color scale while regions of the surgical site that have poor blood flow and thus are supplied with blood late will typically be shown nearer the blue end of the color scale. The artery supplying the blood, which includes the unrepaired aneurysm 502, is shown as being nearer the red end of the color scale, thereby indicating that blood is flowing into the aneurysm 502 via this vessel. In contrast, tissue regions surrounding the artery (e.g., abducent vessels in tissue regions surrounding the artery) are shown as being nearer the blue end of the color scale, thereby indicating later blood flow in those regions. This image can help the surgeon to determine the severity of the aneurysm and the blood supply to the aneurysm.

A high-resolution display of image information is possible by subjecting the individual images to motion compensation and brightness correction techniques of the type described above with regard to FIG. 3.

Figure 5:
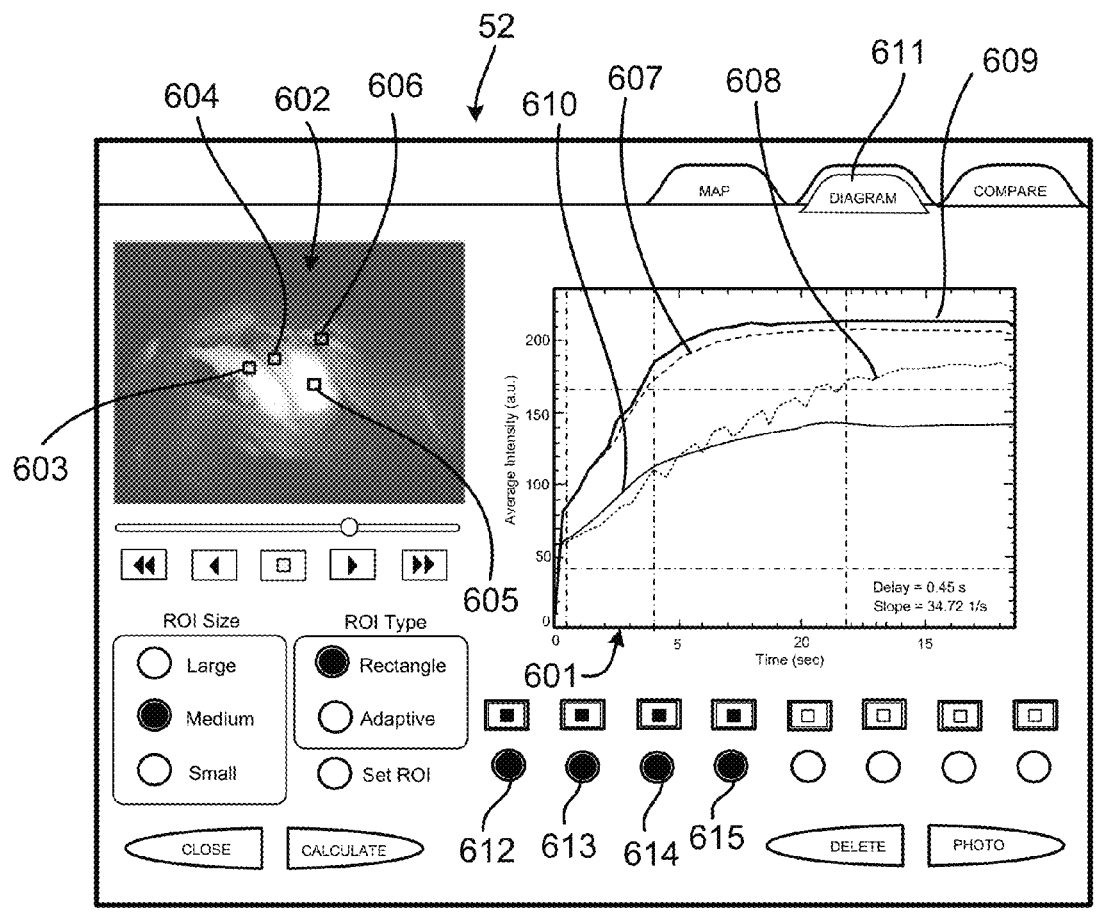
FIG. 5 illustrates the display screen of the operating microscope of FIG. 1, displaying the local changes over time in the fluorescent light intensity at selected points in the blood vessel region shown in FIG. 2.

FIG. 5 is another screen shot of the touch screen 52. As shown, a Diagram tab 611 has been selected, and, as indicated in display field 602, the surgeon has selected regions 603, 604, 605, 606 of the imaged surgical site in order to view the intensity of the fluorescent light over time at those regions of the imaged surgical site. Display field 602 displays the spatial distribution of the fluorescent light intensity at the surgical site and includes boxes over various regions 603, 604, 605, 606 of that image, which indicate regions of the site that the surgeon has chosen to view. The surgeon can select the sites to be viewed by simply touching the portion of the screen that displays the region of the image in which the surgeon is interested. As a result of the selections made by the surgeon, the signal analysis and processing unit 50 analyzes each selected region 603, 604, 605, 606 on the series of images transmitted to it by the fluorescent camera 41 and charts the mean fluorescent light intensity at those regions over time. This information is then transmitted to the touch screen 52 where it is displayed in a display field 601 as intensity characteristics 607, 608, 609 610.

The surgeon can choose which of the regions 603, 604, 605, 606 to view graphs of by selecting buttons 612, 613, 614, 615 on the touch screen 52. While graphs are displayed in the display field 601 for only four selected regions, the surgeon can select up to eight regions and can elect to view graphs of any number of those regions at a given time be selecting or deselecting the buttons on the touch screen that correspond to those regions.

Regions 603, 604, 605, and 606 selected by the surgeon on the display field 602 are regions for analysis. They are stored as individual images from the sequence captured by the camera 41 in the operating microscope 1. In doing so, position-dependent values are determined, where the position to be analyzed, a starting pixel, is selected and an analysis region is defined at this position. The determination of the size and/or form of the analysis region occurs automatically and dependently on the content of the image. The maximum size of the analysis region is predetermined. For example, the maximum diameter of the analysis region can be between 3% and 5% of the side length of the respective image. The maximum number of pixels in an analysis region can also be predefined. The size of an analysis region is based on the edge of the image to be analyzed. The shape of the analysis region follows, at least in some areas, the shape of the image content. The pixels of the analysis region are determined by comparing their value to the value of the start-up pixel. Pixels for the analysis region are selected when the difference between their values and the value of the starting pixel lies within the positional deviation of the pixel values of a defined region. In this respect, the analysis region is a cohesive area, wherein the analysis region is adjusted to every individual image of the image sequence to be analyzed. Before the analyzing regions are defined, a motion compensation is applied to the individual images.

The analysis of the image data in the selected area region on the display field 602 on the display screen is started only after the surgeon has confirmed the selected position. For this purpose, the surgeon must touch the desired area on the display field 602. The selected position is located on the display in the central area of the enlarged section of the image data. The side length of the central area is 50% of the side length of the magnified section. The side length of the central region may also be 25% of the magnified section. In the boundary area of the image data, the central region is moved in the direction of the boundary of the magnified section. In doing so, the image data are analyzed such that the position selected by the surgeon is corrected before it is confirmed. However, an automatic confirmation after the correction is also possible. The surgeon can confirm the position by touching a control field on the display screen. In doing so, the image data can be corrected multiple times. It is, however, advantageous for the position of the image data to be corrected automatically. For this purpose the system, using an object detection routine, the position is moved to the nearest object. The magnified section is then enlarged in several steps.

The time characteristic of the intensity averaged across a selected area visualized on the display field 601 quantifies the blood flow in the selected area sections. This can, for example, help the surgeon to determine the severity of the aneurysm.

After studying the blood flow patterns through the surgical site by reviewing the various images displayed by the touch screen 52 (as shown in FIGS. 3-5) the surgeon can repair the aneurysm with one or more clips.

Figure 6:
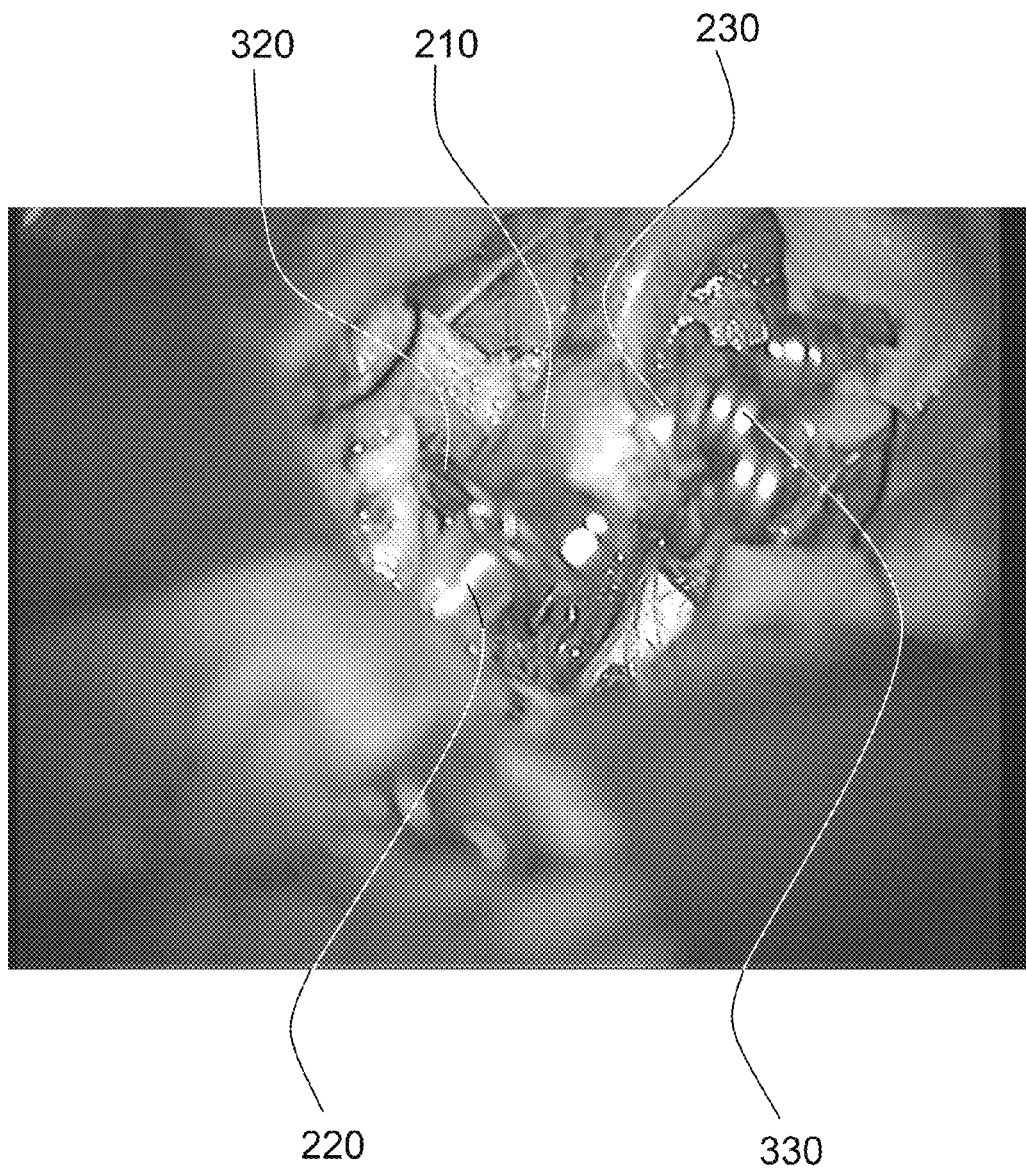
FIG. 6 is an image of the blood vessel region shown in FIG. 2 after performing neuro-surgical therapy to repair the aneurysm.

FIG. 6 shows the surgical site 2, as viewed through operating microscope 1, after placing a clip 320 at the aneurysm sac 210 and the evagination 220, and a clip 330 at the evagination 230 of the aneurysm sac 210.

It is beneficial for the surgeon to verify the success of the aneurysm repair during the surgery. The surgeon can, for example, verify the success of the aneurysm surgery by determining (1) if the aneurysm is eliminated or greatly reduced by the clips 320, 330, (2) if arterial blood continues to flow into the aneurysm sac 210 and its evaginations 220, 230 despite the applied clips 320, 330, and/or (3) if the blood flow through the artery is constricted or even interrupted by the clips 320, 330. In order to make these determinations, the techniques described above with respect to FIGS. 3-5 can be repeated after the clips 320, 330 have been positioned about the aneurysm. This allows the surgeon to view the blood flow patterns at the surgical site after repair of the aneurysm, and thus assess the efficacy of the treatment.

The operating microscope 1 also offers the surgeon the option to simultaneously display (on the touch screen 52) images related to blood flow patterns at the surgical site 2 prior to repairing the aneurysm and images related to blood flow patterns at the surgical site 2 after repairing the aneurysm. This enables the surgeon to assess the success of the aneurysm surgery based on the displayed information on a single display screen.

Figure 7:
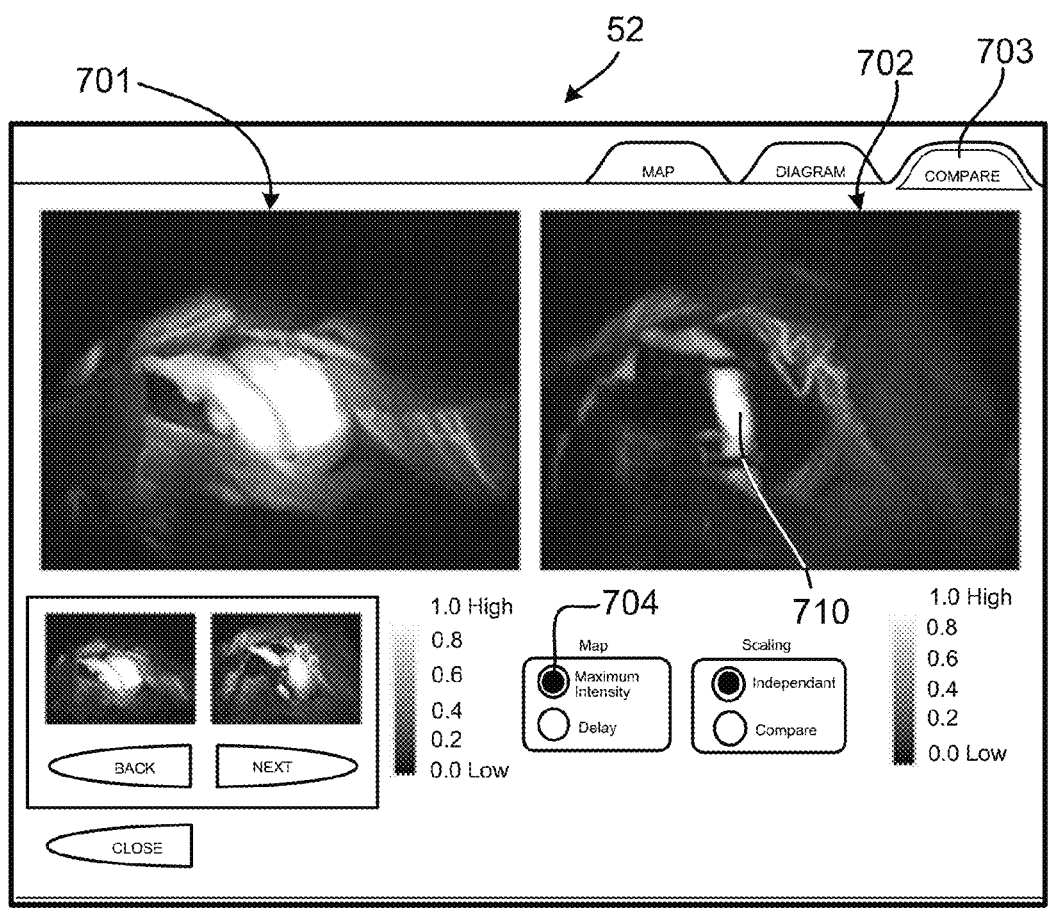
FIG. 7 illustrates the display screen of the operating microscope of FIG. 1, displaying a comparison of the spatial distribution of a maximum intensity of fluorescent light intensity in the blood vessel region shown in FIGS. 2 and 6 before and after repair of the aneurysm.

FIG. 7 is a screen shot of the touch screen 52 with a display field 701 showing the spatial distribution of the fluorescent light intensity at the surgical site before the aneurysm was repaired and a display field 702 showing the spatial distribution of the fluorescent light intensity at the surgical site after the aneurysm was repaired. As shown, the surgeon has accessed this screen by pressing a Compare tab 703 and has opted to view the maximum intensity at the surgical site by pressing a Maximum Intensity button 704. The spatial distribution of the fluorescent light intensity is obtained and displayed using the procedure described above with respect to FIG. 3. In particular, the procedure described with respect to FIG. 3 is repeated after repairing the aneurysm such that the operating microscope 1 collects sufficient data to display the spatial distribution of the fluorescent light intensity at the surgical site before and after the aneurysm repair. From the touch screen 52 shown in FIG. 7, the surgeon can quickly determine that due to the clips, the area 710 of the surgical field, which originally contained the aneurysm, no longer receives blood. This indicates that the aneurysm was successfully treated with the aneurysm surgery.

Figure 8:
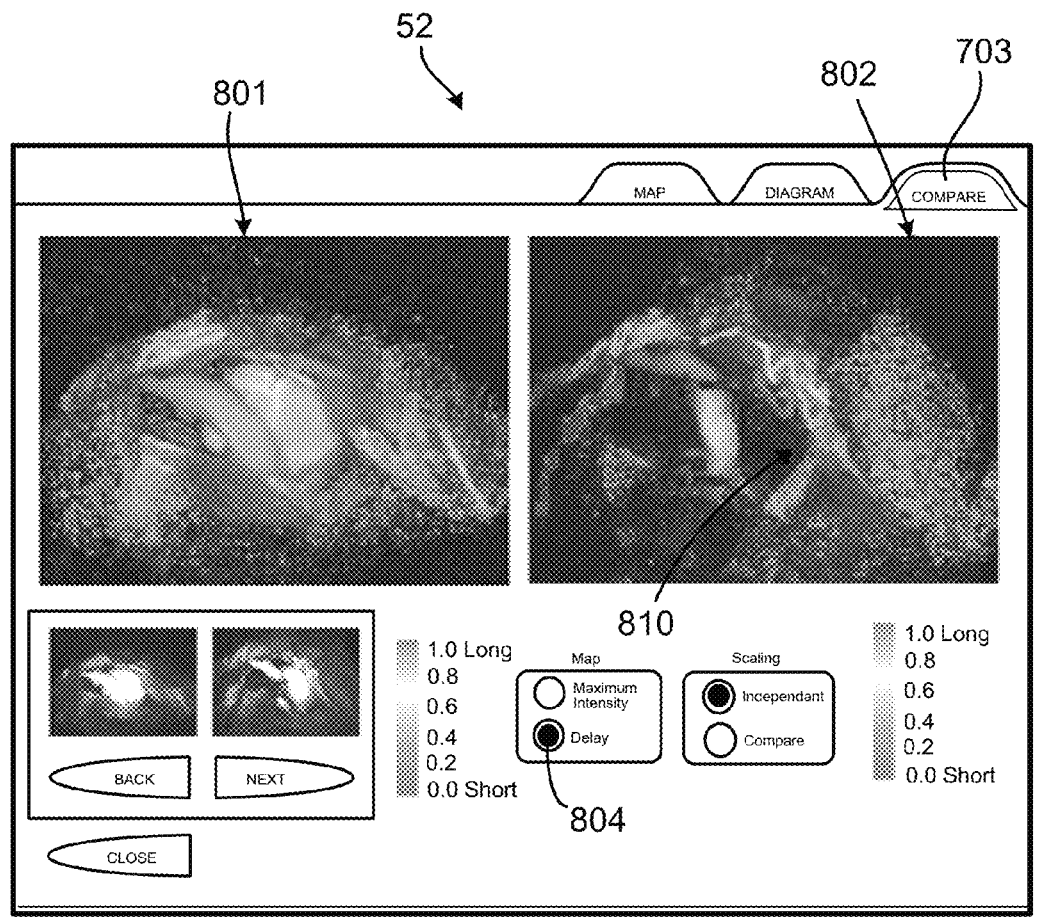
FIG. 8 illustrates the display screen of the operating microscope of FIG. 1, displaying the comparison of images representing the different rates at which the fluorescent light intensity changes over time in the blood vessel region shown in FIGS. 2 and 6 before and after repair of the aneurysm.

FIG. 8 is a screen shot of the touch screen 52 with a display field 801 showing the spatial distribution of the rate at which the fluorescent light intensity at the various different points of the surgical site reached a threshold intensity value before the aneurysm was repaired and with a display field 802 showing the spatial distribution of the rate at which the fluorescent light intensity at the various different points of the surgical site reached the threshold intensity value after the aneurysm was repaired. As shown, the surgeon has accessed this screen by pressing the Compare tab 703 and has opted to view the time required to reach the threshold intensity value at each of the various points by pressing a Delay button 804. The spatial distribution of the time required for the various points to reach the threshold intensity value is obtained with the procedure described with respect to FIG. 4. In particular, the procedure described with respect to FIG. 4 is repeated after repairing the aneurysm such that the operating microscope 1 collects sufficient data to display the spatial distribution of the time required for each of the points at the surgical site to reach the threshold intensity value before and after the aneurysm repair. From the display screen shown in FIG. 8 the surgeon can determine that due to the applied clips blood is not allowed to flow into area 810 of the surgical field, not even with a delay. Again, this allows the surgeon to conclude that the aneurysm surgery in this area was successful.

Figure 9:
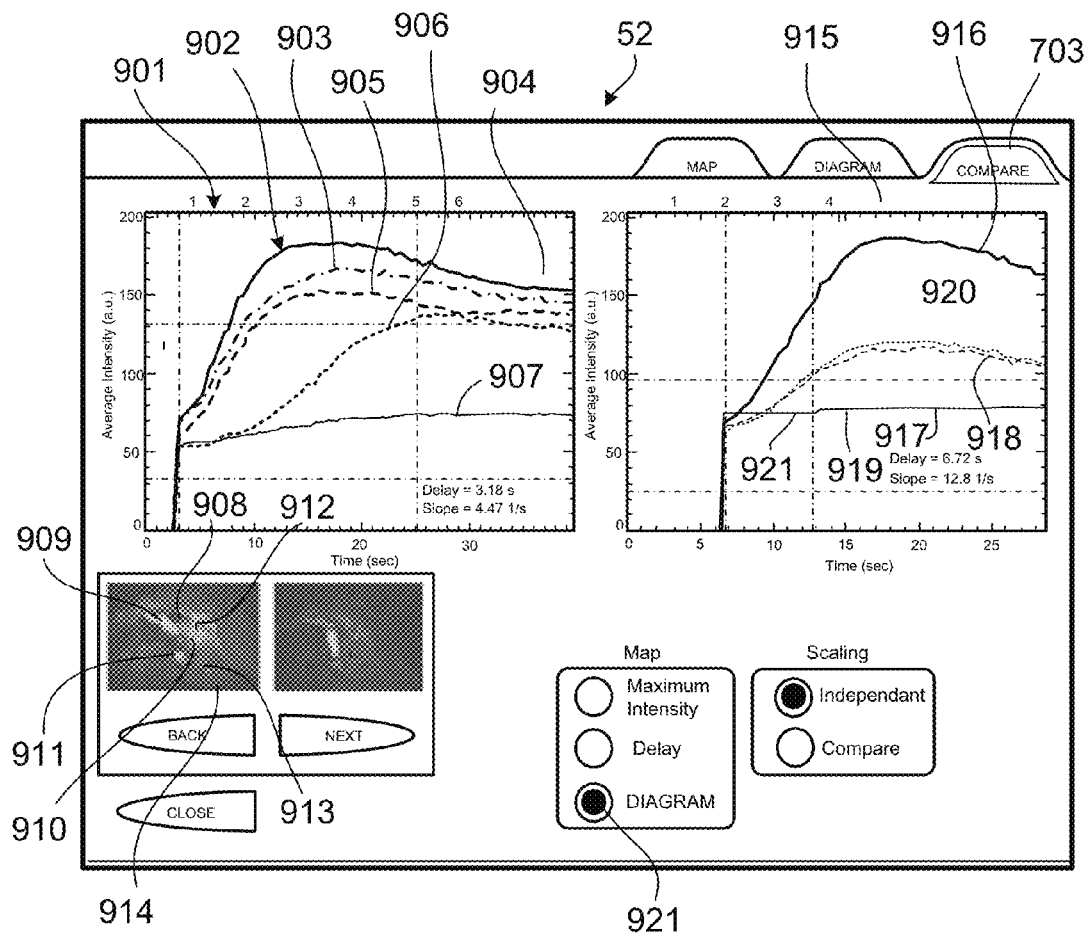
FIG. 9 illustrates the display screen of the operating microscope of FIG. 1, displaying the comparison of the local changes over time in the fluorescent light intensity at selected points in the blood vessel region shown in FIGS. 2 and 6 before and after repair of the aneurysm.

FIG. 9 is a screen shot of the touch screen 52 with a display field 901 showing graphs 902, 903, 904, 905, 906, and 907 that represent the local time characteristic of the fluorescent light intensity at tissue regions 908, 909, 910, 911, 912 and 913 of the surgical site, which is shown in a display field 914, before repair of the aneurysm. A display field 915 similarly shows graphs 916, 917, 918, 919, 920, and 921 that represent the local time characteristic of the fluorescent light intensity at tissue regions 908, 909, 910, 911, 912 and 913 of the surgical site after repair of the aneurysm. As shown, the surgeon has accessed this screen by pressing the Compare tab 703 and has opted to view graphs of the intensity at the selected regions of the surgical site by pressing a Diagram button 921. Graphs 902-907 are obtained with the procedure described above with respect to FIG. 5. In particular, the procedure described with respect to FIG. 5 is repeated after repairing the aneurysm such that the operating microscope 1 collects sufficient data to display the local time characteristic of the fluorescent light intensity at the selected tissue regions of the surgical site before and after the aneurysm repair. The information provided in display fields 901 and 915 allows the surgeon to assess the success of the aneurysm surgery. In particular, the comparison of the characteristics of the fluorescent light intensity graphs over time allows the surgeon to determine the local change in blood flow at the surgical site. As a result, it is possible for the surgeon to detect any undesired stenosis, i.e., constrictions of the blood vessels, caused by the application of the clips to the aneurysm. Conventional visualization procedures for structures at a surgical site are typically not able to detect this type of stenosis.

The procedures described herein can be performed especially advantageously with an operating microscope of the type shown in FIG. 1, which allows the surgeon to view the surgical site with the operating microscope throughout the entire aneurysm surgery without having to move the microscope away from the surgical site in order to make room for other diagnostic devices.

While certain embodiments have been described, other embodiments are possible.

In some embodiments, the explained procedure for the treatment of an aneurysm is performed several times in a row. If, for example, in the first attempt the surgeon was unable to clamp off the aneurysm with the clip or if the patient's blood flow is negatively affected, then the surgeon can remove the clip, re-apply it, and check the effect based on the explained procedure.

While the maximum fluorescent light intensity has been described as being shown as a particular brightness, the maximum fluorescent light intensity can alternatively or additionally be displayed as a color. The different maximum fluorescent intensities at the surgical site can, for example, be displayed as different colors along a color scale.

Similarly, while the amount of time for the various different points at the surgical site to reach the predetermine threshold fluorescent light intensity value has been described as being shown as a particular color, this can alternatively or additionally be displayed as a brightness. The different times required to reach the threshold intensity value can, for example, be displayed as different levels of brightness along a brightness scale.

While color scales described herein for displaying different blood flow patterns range from red to blue, any of various other color scales can alternatively be used. In certain embodiments, for example, the color scale progresses from red to yellow to green to blue. For example, those points that required the shortest periods of time to reach the threshold intensity value can be displayed as blue, those points that required the longest periods of time to reach the threshold intensity value can be displayed as red, and those points that required intermediary periods of time to reach the threshold intensity value can be displayed as various shades of yellow or green.

While certain methods described above include introducing ICG into the blood vessel of the patient, any of various other fluorescent dyes can alternatively or additionally be used. In some embodiments, for example, BL is used. In such embodiments, the operating microscope 1 is adjusted to allow for the detection of the fluorescent light emitted by the BL. The filter disk 22 of the lighting system 10 can, for example, be rotated so that the bandpass filter 25 is positioned in the beam of light 12 emitted by the lamp 11.

While certain methods described above include performing neuro-surgical therapy to repair a brain aneurysm, the methods can alternatively or additionally include the performance of other techniques, such as endovascular therapy, to repair the brain aneurysm.

While certain methods described above relate to treating and assessing treatment of a brain aneurysm, the methods can alternatively be used for treating and assessing treatment of aneurysms in various other parts of the body.

Similarly, while certain methods described above relate to treating and assessing treatment of aneurysms, the methods can alternatively or additionally be used to treat and assess treatment of various other medical conditions. For example, the methods described herein can be used for bypass surgeries, stent implantations, arterial venous malformation (AVM) therapies, determining arterial venous transmission time, or any of various other medical treatments in which the flow of blood may be affected.

While certain methods described above relate to assessing fluid flow patterns in a blood vessel, the methods can alternatively or additionally be used to assess fluid flow through other types of body vessels. Examples of other types of body vessels in which the methods can be used are urethras and bowels.

While certain devices of the operating microscope 1 have been described as including actuators that automatically adjust those devices, the operating microscope 1 can alternatively or additionally be configured so that those devices can be manually adjusted.

While the operating microscope 1 has been described as including a Xenon lamp, any of various other light sources can alternatively or additionally be used. Examples of other light sources include halogen lamps, LED lamps, and mercury lamps.

While operating microscope 1 has been described as including a touch screen, any of various other types of monitors, including monitors with hard keypads, can be used.

Other embodiments are within the scope of the following claims.

What is claimed is:

1. A method, comprising:
   recording a first plurality of images of a plurality of points of at least one blood vessel, each of the plurality of images comprising fluorescent light intensity information at each of the plurality of points of the at least one blood vessel;
   for each of the plurality of points of the at least one blood vessel, analyzing the first plurality of recorded images to determine a maximum fluorescent light intensity at the point of the at least one blood vessel; and
   for each of the plurality of points of the at least one blood vessel, displaying a first image that represents the maximum fluorescent light intensity at the point of the at least one blood vessel.

2. The method of claim 1, wherein the at least one blood vessel comprises multiple blood vessels.

3. The method of claim 2, further comprising, after displaying the first image:
   recording a second plurality of images of a plurality of points of the multiple blood vessels, each of the second plurality of images comprising fluorescent light intensity information at each of the plurality of points of the multiple blood vessels;
   for each of the plurality of points of the multiple blood vessels, analyzing the second plurality of recorded images to determine a second fluorescent light intensity at the point of the multiple blood vessels; and
   for each of the plurality of points of the multiple blood vessels, displaying a second image that represents the second maximum fluorescent light intensity at the point of the multiple blood vessels.

4. The method of claim 3, further comprising simultaneously displaying the first and second images.

5. The method of claim 4, wherein the first and second images are displayed in a side-by-side fashion.

6. The method of claim 5, further comprising repairing an aneurysm at the multiple blood vessels.

7. The method of claim 6, further comprising:
   before recording the first plurality of images, injecting a fluorescent dye into the multiple blood vessels;
   after injecting the fluorescent dye into the multiple blood vessels, applying a clip to the aneurysm to clamp off the aneurysm; and
   after applying the clip to the aneurysm, capturing the second set of images.

8. The method of claim 3, further comprising repairing an aneurysm at the multiple blood vessels.

9. The method of claim 8, wherein the first image is displayed before repairing the aneurysm at the multiple blood, vessels, and the second image is displayed after repairing the aneurysm at the multiple blood vessels.

10. The method of claim 9, further comprising:
    before recording the first plurality of images, injecting a fluorescent dye into the multiple blood vessels;
    after injecting the fluorescent dye into the multiple blood vessels, applying a clip to the aneurysm to clamp off the aneurysm; and
    after applying the clip to the aneurysm, capturing the second set of images.

11. The method of claim 8, further comprising:
    before recording the first plurality of images, injecting a fluorescent dye into multiple blood vessels;
    after displaying the first image, applying a clip to the aneurysm to clamp off the aneurysm; and
    after applying the clip to the aneurysm, capturing the second set of images.

12. The method of claim 1, further comprising, after displaying the first image:
    recording a second plurality of images of the plurality of points of the at least one blood vessel, each of the second plurality of images comprising fluorescent light intensity information at each of the plurality of points of the at least one blood vessel;
    foe each of the plurality of points of the at least one blood vessel, analyzing the second plurality of recorded images to determine a second maximum fluorescent light intensity at the point of the at least one blood vessel; and
    for each of the plurality of points of the at least one blood vessel, displaying a second image that represents the second maximum fluorescent light intensity at the point of the at least one blood vessel.

13. The method of claim 12, further comprising simultaneously displaying the first and second images.

14. The method of claim 13, wherein the first and second images are displayed in a side-by-side fashion.

15. The method of claim 14, further comprising repairing an aneurysm at the at least one blood vessel.

16. The method of claim 15, further comprising:
    before recording the first plurality of images, injecting a fluorescent dye into the at least one blood vessel;
    after injecting the fluorescent dye into the at least one blood vessel, applying a clip to the aneurysm to clamp off the aneurysm; and
    after applying the clip to the aneurysm, capturing the second set of images.

17. The method of claim 12, further comprising repairing an aneurysm at the at least one blood vessel.

18. The method of claim 17, wherein the first image is displayed before repairing the aneurysm at the at least one blood vessel, and the second image is displayed after repairing the aneurysm at the at least one blood vessel.

19. The method of claim 18, further comprising:
before recording the first plurality of images, injecting a fluorescent dye into the at least one blood vessel;
after injecting the fluorescent dye into the at least one blood vessel, applying a clip to the aneurysm to clamp off the aneurysm; and
after applying the clip to the aneurysm, capturing the second set of images.

20. The method of claim 17, further comprising:
before recording the first plurality of images, injecting a fluorescent dye into the at least one blood vessel;
after injecting the fluorescent dye into the at least one blood vessel, applying a clip to the aneurysm to clamp off the aneurysm; and
after applying the clip to the aneurysm, capturing the second set of images.

\* \* \* \* \*